(12) United States Patent
Lee et al.

(10) Patent No.: US 8,461,236 B2
(45) Date of Patent: Jun. 11, 2013

(54) PHOSPHORIC COMPOUND, METHOD FOR PREPARING THE SAME, AND FLAME RETARDANT THERMOPLASTIC RESIN COMPOSITION INCLUDING THE SAME

(75) Inventors: Min Soo Lee, Anyang-Si (KR); Beom Jun Joo, Seoul-Si (KR)

(73) Assignee: Cheil Industries Inc., Gumi-si (KR)

( * ) Notice: Subject to any disclaimer, the term of this patent is extended or adjusted under 35 U.S.C. 154(b) by 0 days.

(21) Appl. No.: 13/151,616

(22) Filed: Jun. 2, 2011

(65) Prior Publication Data

US 2011/0263768 A1    Oct. 27, 2011

Related U.S. Application Data

(63) Continuation-in-part of application No. PCT/KR2009/001975, filed on Apr. 16, 2009.

(30) Foreign Application Priority Data

Dec. 9, 2008  (KR) .................. 10-2008-0124486

(51) Int. Cl.
*C08K 5/5333*    (2006.01)
(52) U.S. Cl.
USPC ............ 524/130; 524/126; 524/127; 524/133
(58) Field of Classification Search
USPC .................. 524/130, 126, 127, 133
See application file for complete search history.

(56) References Cited

U.S. PATENT DOCUMENTS

| 4,152,373 A | 5/1979 | Honig et al. |
| 2009/0088501 A1* | 4/2009 | Qiu et al. .................... 524/100 |

FOREIGN PATENT DOCUMENTS

| JP | 57-105435 | * | 6/1982 |
| JP | 57-105435 A | | 6/1982 |
| WO | 2010/067926 A1 | | 6/2010 |

OTHER PUBLICATIONS

International Search Report in counterpart International Application No. PCT/KR2008/001975 dated Jul. 1, 2010, pp. 1-4.
McWhirter et al., "Mechanistic Study of Protein Phosphatase-1 (PP1), A Catalytically Promiscuous Enzyme," Am. Chem. Soc., 2008, 130, No. 41. pp. 13673-13682.

* cited by examiner

*Primary Examiner* — Peter Szekely
(74) *Attorney, Agent, or Firm* — Summa, Additon & Ashe, P.A.

(57) ABSTRACT

The present invention provides a novel phosphoric compound, a method for preparing the same, and a thermoplastic resin composition including the same. A thermoplastic resin composition comprising the phosphoric compound of the present invention can have excellent flame retardancy, and can be eco-friendly because the phosphoric compound does not generate toxic gas during molding or combustion.

21 Claims, 6 Drawing Sheets

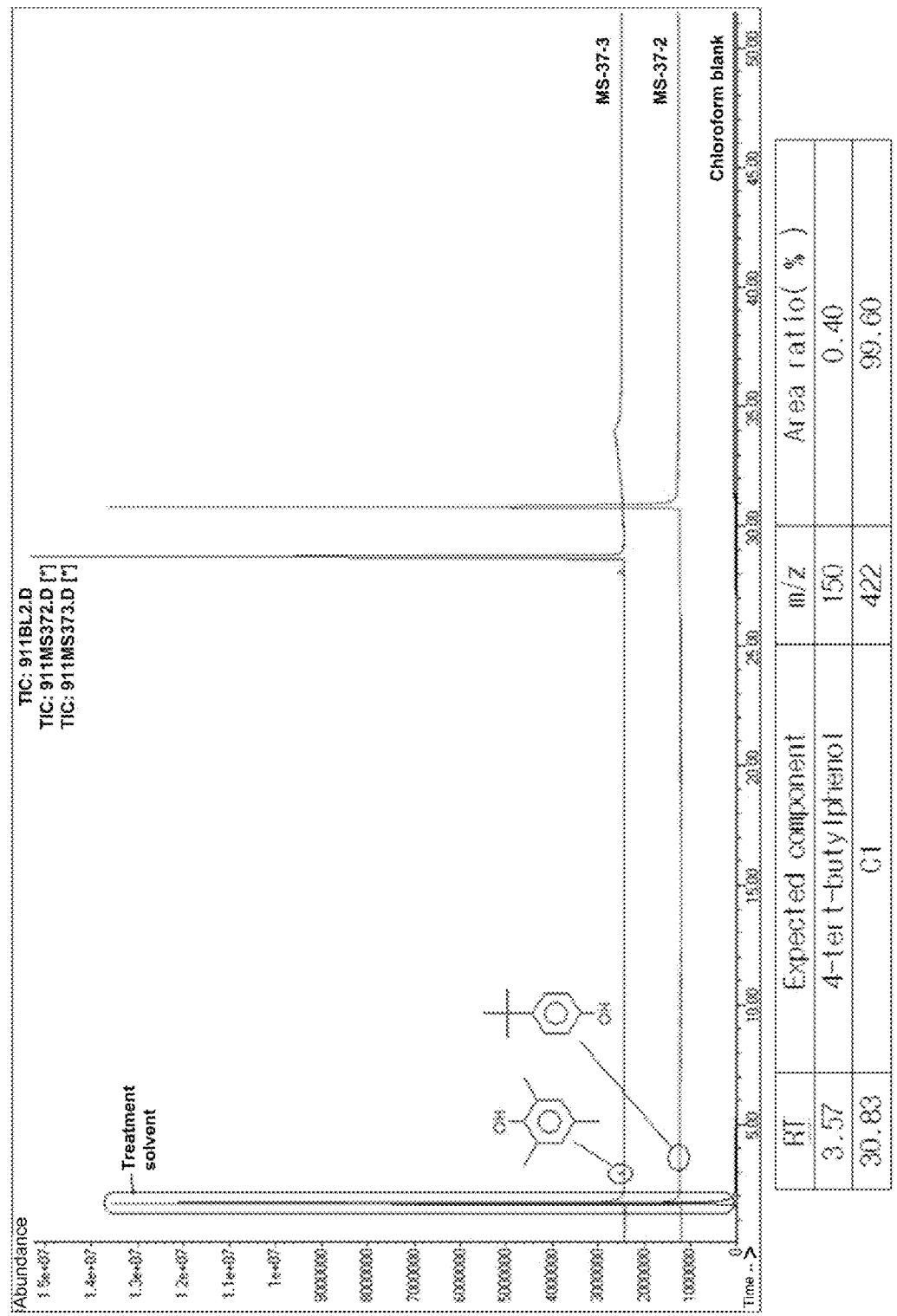

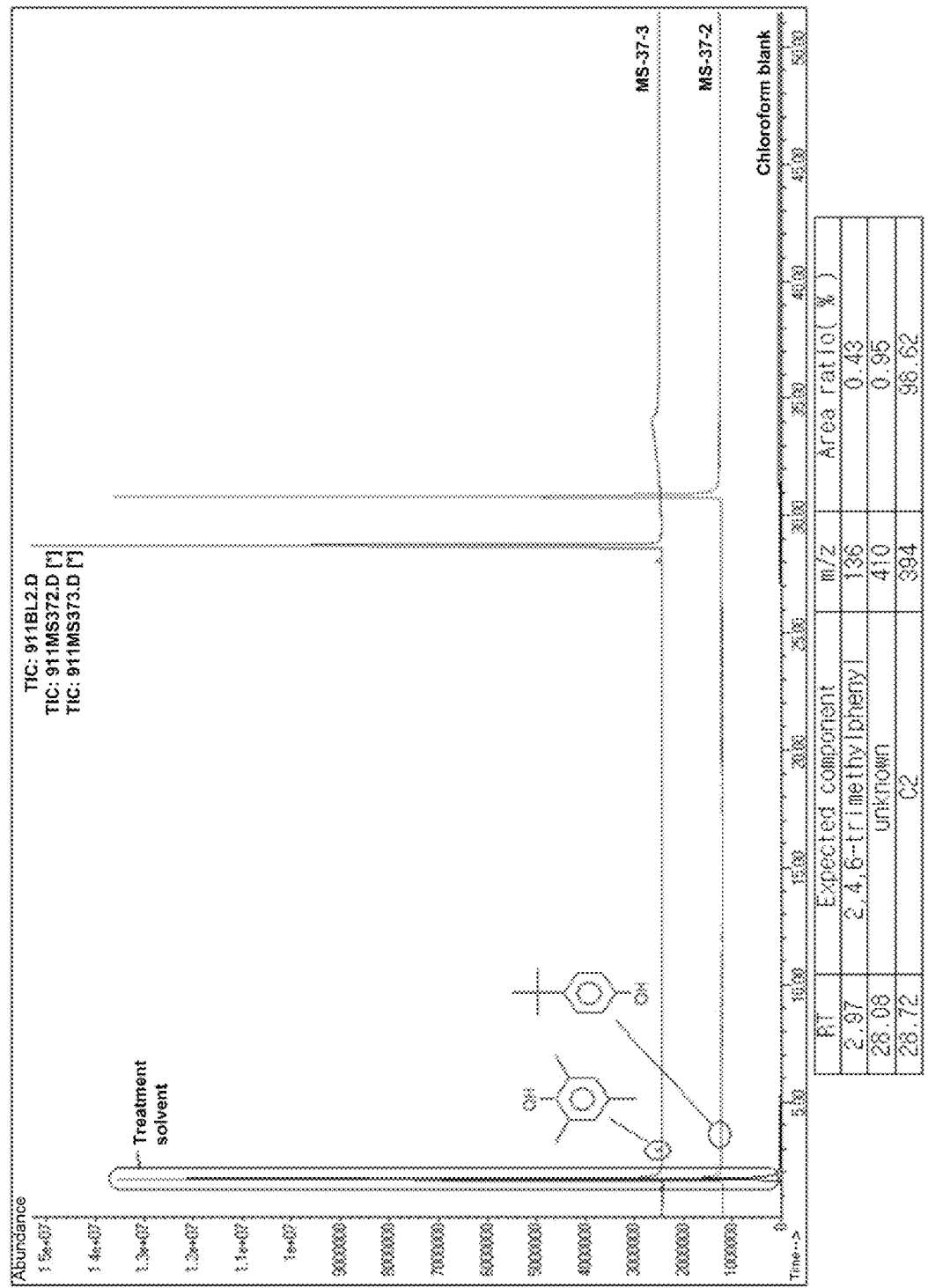

PHOSPHORIC COMPOUND, METHOD FOR PREPARING THE SAME, AND FLAME RETARDANT THERMOPLASTIC RESIN COMPOSITION INCLUDING THE SAME

CROSS-REFERENCE TO RELATED APPLICATIONS

This application is a continuation-in-part of International Application No. PCT/KR2009/001975, filed Apr. 16, 2009, pending, which designates the U.S., published as WO 2010/067926, and is incorporated herein by reference in its entirety, and claims priority therefrom under 35 USC Section 120. This application also claims priority under 35 USC Section 119 from Korean Patent Application No. 10-2008-0124486, filed Dec. 9, 2008, in the Korean Intellectual Property Office, the entire disclosure of which is also incorporated herein by reference.

FIELD OF THE INVENTION

The present invention relates to a novel phosphoric compound, method for preparing the same, and flame retardant thermoplastic resin composition using the same.

BACKGROUND OF THE INVENTION

Thermoplastic resins can have excellent processability and mechanical properties and accordingly are used in the production of a variety of molded products. However, the thermoplastic resins can be easily burned by ignition sources and can spread fire. Therefore, thermoplastic resins used in housings of electronic heat-emitting products such as computers, facsimiles, and the like, should be treated to impart flame retardancy thereto.

Conventionally, a halogen-containing compound and an antimony-containing compound had been added to thermoplastic resins to impart flame retardancy. Examples of halogen-containing compounds include polybromodiphenyl ether, tetrabromobisphenol-A, epoxy compounds substituted with bromine, chlorinated polyethylene, and the like. Examples of the antimony-containing compounds include antimony trioxide and antimony pentoxide.

A halogen-containing compound and antimony-containing compound can impart flame retardancy to a thermoplastic resin with minimal deterioration of the physical properties thereof. Halogen-containing compounds such as polybromodiphenyl ether, however, can generate toxic hydrogen halide gases during molding processes. Therefore, there is an increased need for improving flame retardancy of thermoplastic resins without using halogen-containing compounds.

Phosphoric ester compounds can be used as a flame retardant for thermoplastic resins instead of a halogen-containing flame retardant. However, typically the phosphoric ester flame retardant must be used in such a large amount to provide adequate flame retardancy, which can negatively impact other physical properties of the thermoplastic resin.

SUMMARY OF THE INVENTION

Accordingly, in order to solve the problems of conventional phosphoric flame retardants, the present inventors have developed a novel phosphoric compound which can exhibit improved flame retardancy as compared to conventional phosphoric ester flame retardants. The novel phosphoric compound of the invention also does not generate toxic hydrogen halide gases.

The inventors have also developed a non-halogen compound containing flame retardant thermoplastic resin composition that can have excellent flame retardancy, which includes the novel phosphoric compound as a flame retardant. The composition of the invention can be more eco-friendly than conventional compositions including a halogen-containing flame retardant because the composition does not generate hydrogen halide gases during processing or combustion of the resin composition. In exemplary embodiments, the thermoplastic resin composition can include an aromatic vinyl polymer resin and a polyphenylene ether resin, which embodiment can also exhibit good moldability as well flame retardancy because the amount of polyphenylene ether resin used can be reduced.

The phosphoric compound of the invention is represented by the following Chemical Formula 1:

[Chemical Formula 1]

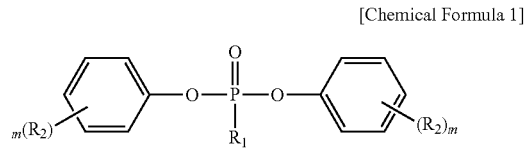

wherein $R_1$ and $R_2$ are the same or different and are independently $C_1$-$C_6$ alkyl or aryl; and each m is the same or different and is independently an integer of 1 to 3.

In exemplary embodiments of the present invention, $R_1$ may be phenyl and each $R_2$ may be $C_1$-$C_6$ alkyl.

In exemplary embodiments of the present invention, the phosphoric compound may be bis(4-tert-butylphenyl)phenyl phosphonate or bis(2,4,6-trimethylphenyl)phenyl phosphonate.

The present invention also provides a method for preparing the phosphoric compound represented by Chemical Formula 1. The method comprises reacting a compound, or a combination of compounds, represented by following Chemical Formula 4 with a compound represented by following Chemical Formula 5 in the presence of an organic amine compound.

[Chemical Formula 4]

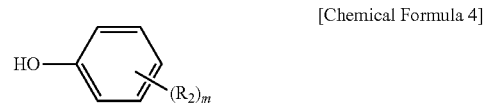

In Chemical Formula 4, each $R_2$ is independently $C_1$-$C_6$ alkyl or aryl; and m is an integer of 1 to 3.

[Chemical Formula 5]

In Chemical Formula 5, $R_1$ is $C_1$-$C_6$ alkyl or aryl.

In exemplary embodiments of the present invention, the organic amine compound may be pyridine, triethylamine, or mixture thereof.

In exemplary embodiments of the present invention, the molar ratio of the compound represented by Chemical Formula 4 to the compound represented by Chemical Formula 5 can be about 2:1 to about 3:1.

In exemplary embodiments of the present invention, the reaction molar ratio of the organic amine compound to the compound represented by Chemical Formula 5 can be about 2:1 to about 50:1.

In exemplary embodiments of the present invention, the method comprises the following steps: reacting the compound represented by Chemical Formula 4 with the compound represented by Chemical Formula 5 in the presence of an organic amine compound for about 10 to about 30 hours at a temperature of about 120 to about 160° C. while stirring and refluxing the reaction mixture; removing unreacted organic amine compound by depressurizing the reaction product obtained by the reaction; and filtering and drying the reaction product, from which the unreacted organic amine compound was removed, after washing the reaction product.

The present invention further provides to a flame retardant comprising the phosphoric compound represented by Chemical Formula 1.

The present invention also provides a flame retardant thermoplastic resin composition including the phosphoric compound represented by Chemical Formula 1 or a mixture thereof. In exemplary embodiments of the present invention, the composition comprises about 0.5 to about 30 parts by weight of the phosphoric compound represented Chemical Formula 1 or a mixture thereof, based 100 parts by weight of the thermoplastic resin.

In exemplary embodiments of the present invention, the phosphoric compound may be bis(4-tert-butylphenyl)phenylphosphonate, bis(2,4,6-trimethylphenyl)phenylphosphonate, or a mixture thereof.

The thermoplastic resin is especially not limited. In exemplary embodiments of the present invention, the thermoplastic resin may include an aromatic vinyl polymer resin, polyphenylene ether resin, polyphenylene sulfide resin, polycarbonate resin, polyolefin-based resin, polyester, polyamide, and the like. The thermoplastic resin may be used alone or in combination thereof.

In exemplary embodiments of the present invention, the thermoplastic resin may include (A) about 80 to about 95% by weight of an aromatic vinyl polymer resin and (B) about 5 to about 20% by weight of a polyphenylene ether resin.

In exemplary embodiments of the present invention, the thermoplastic resin may further include a flame retardant including (D1) an aromatic phosphoric acid ester compound, (D2) an alkyl phosphinic acid metal salt compound, or a mixture thereof. In exemplary embodiments of the present invention, the composition can include about 1 to about 25 parts by weight of (D1) the aromatic phosphoric acid ester compound, (D2) the alkyl phosphinic acid metal salt compound, or a mixture thereof, based on 100 parts by weight of the thermoplastic resin.

In exemplary embodiments of the present invention, the resin composition may further comprise one or more additives such as a plasticizer, heat stabilizer, oxidation inhibitor, anti-dripping agent, compatibilizer, light stabilizer, pigment, dye, inorganic filler, and the like, and combinations thereof.

In exemplary embodiments of the present invention, the first average combustion time of the resin composition measured in accordance with the UL 94 VB for specimens having a thickness of about 1/8" can be less than 38 seconds.

DETAILED DESCRIPTION OF THE INVENTION

Figure 1:
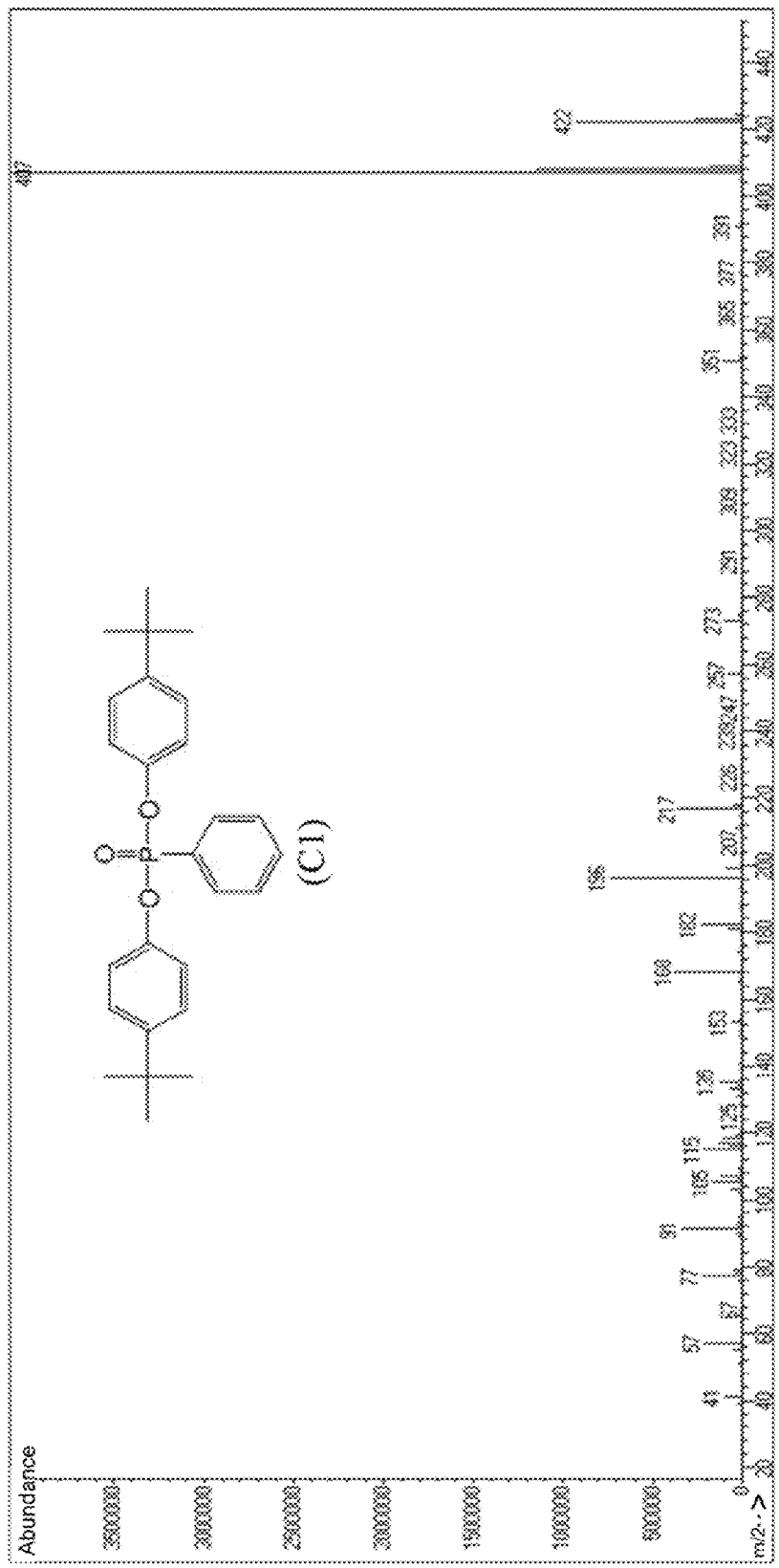
FIG. 1 is a GC-MS chromatogram of phosphoric compound (C1) prepared in Example 1.

The present invention will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

Phosphoric Compound

A phosphoric compound of the present invention is represented by the following Chemical Formula 1.

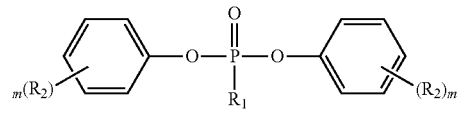

[Chemical Formula 1]

In Chemical Formula 1, $R_1$ and $R_2$ are the same or different and are independently $C_1$-$C_6$ alkyl or aryl; and each m is the same or different and are independently an integer of 1 to 3.

The $C_1$-$C_6$ alkyl may be linear or branched. Unless otherwise defined, as used herein, the term "aryl" refers to $C_6$-$C_{20}$ aryl or $C_1$-$C_6$ alkyl-substituted $C_6$-$C_{20}$ aryl.

In exemplary embodiments of the present invention, $R_1$ may be phenyl and each $R_2$ may be $C_1$-$C_6$ alkyl. For example, each $R_2$ can be $C_1$-$C_2$ alkyl and each m can be 2 or 3, for example 3.

In exemplary embodiments, $R_1$ is phenyl, each $R_2$ is branched $C_3$-$C_6$ alkyl, for example tert-butyl, and m is 1. Exemplary embodiments of the phosphoric compound represented by the Chemical Formula 1 include without limitation bis(4-tert-butylphenyl)phenyl phosphonate represented by the following Chemical Formula 2 and bis(2,4,6-trimethylphenyl)phenyl phosphonate represented by the following Chemical Formula 3.

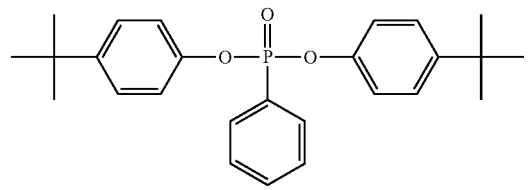

[Chemical Formula 2]

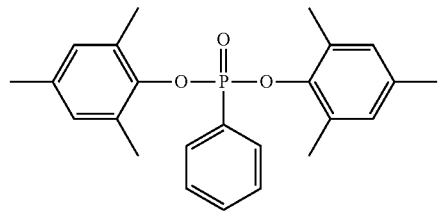

[Chemical Formula 3]

Method for Preparing the Phosphoric Compound

The phosphoric compound of the present invention can be prepared by reacting the compound, or a combination of compounds, represented by Chemical Formula 4 with the compound represented by Chemical Formula 5 in the presence of an organic amine compound as shown in the following Reaction Equation 1. Specifically, the phosphoric compound of the Chemical Formula 1 can be prepared by dehydrochlorination reaction of the compound represented by Chemical Formula 4 and the compound represented by Chemical Formula 5.

[Reaction Equation 1]

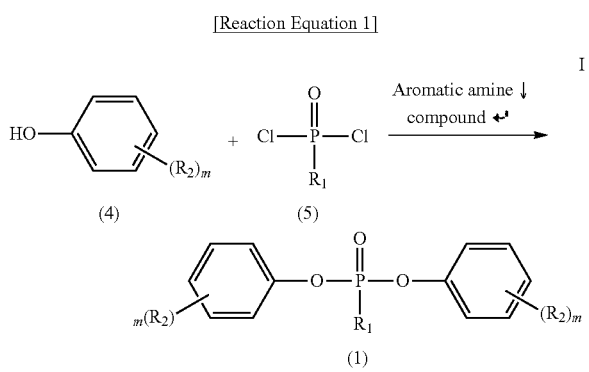

In Reaction Equation 1, each $R_1$ and $R_2$ is independently $C_1$-$C_6$ alkyl or aryl as defined herein; and m is an integer of 1 to 3.

Exemplary compounds represented by Chemical Formula 4 may include, but are not limited to, 4-tert-butyl phenol, 2,4,6-trimethyl phenol, and the like, and combinations thereof. Exemplary compounds represented by Chemical Formula 5 may include, but are not limited to, phenylphosphonic dichloride.

The organic amine compound promotes the dehydrochlorination reaction, removes HCl, which is a by-product of the dehydrochlorination reaction, and at the same time works like solvent. Exemplary embodiments of the organic amine compound may include, but are not limited to, pyridine, triethylamine, and the like, and mixtures thereof.

In exemplary embodiments of the present invention, a reaction molar ratio of the compound represented by Chemical Formula 4 to the compound represented by Chemical Formula 5 may be about 2:1 or more. In other exemplary embodiments of the present invention, a reaction molar ratio of the compound represented by Chemical Formula 4 to the compound represented by Chemical Formula 5 may be about 2:1. However, because some of the compounds represented by Chemical Formula 4 may not participate in the reaction due to vaporization during reaction, the reaction molar ratio of the compound represented by Chemical Formula 4 to the compound represented by Chemical Formula 5 may be about 2:1 or more, for example about 2:1 to about 3:1 to prevent this problem.

The organic amine compound may be used in an excess amount based on 1 mole of the compound represented by Chemical Formula 5. In exemplary embodiments, the reaction molar ratio of the organic amine compound to the compound represented by Chemical Formula 5 may be about 2:1 to about 50:1, for example, the reaction molar ratio of the organic amine compound to the compound represented by Chemical Formula 5 may be about 2:1 to about 10:1. When the organic amine compound is used in an amount of less than about 2 moles based on 1 mole of the compound represented by Chemical Formula 5, the dehydrochlorination reaction may not proceed smoothly and it can be difficult to remove HCl by-product. Although the maximum value of the reaction molar ratio of the organic amine compound to the compound represented by Chemical Formula 5 is not particularly limited, typically the invention will not exceed 50 molar ratio to reduce manufacturing costs and costs for collecting unreacted organic amine compound.

In exemplary embodiments of the present invention, the method comprises: reacting the compound, or a combination of compounds, represented by Chemical Formula 4 with the compound represented by Chemical Formula 5 at a temperature of about 120 to about 160° C. for about 10 to about 30 hours, for example about 20 to about 27 hours, while stirring and refluxing the reaction mixture.

In exemplary embodiments of the present invention, the compound, or a combination of compounds, represented by Chemical Formula 4 can be reacted with the compound represented by Chemical Formula 5 while stirring and refluxing the reaction mixture, and then the phosphoric compound represented by Chemical Formula 1 can be formed by the dehydrochlorination reaction as mentioned above. HCl, which is a by-product of the dehydrochlorination reaction, can bond with the organic amine compound and thereby form an organic amine hydrochloride.

In another exemplary embodiment of the present invention, the method may further comprise removing the unreacted organic amine compound and the organic amine hydrochloride from the reaction product obtained by the dehydrochlorination reaction.

The unreacted organic amine compound can be removed by depressurizing the reaction product including the phosphoric compound represented by Chemical Formula 1, the organic amine hydrochloride and the unreacted organic amine compound. In this case, the reaction product can be depressurized using a rotary distillation apparatus at room temperature.

After the unreacted organic amine compound is removed by the depressurizing process, the reaction product can be washed filtered and dried. For example, water can be added to the reaction product, from which the unreacted organic amine compound is removed, the resulting solution can be stirred for about 0.5 to about 2 hours and filtered, the organic amine hydrochloride present in the reaction product can be dissolved in water and removed, and the phosphoric compound represented by Chemical Formula 1, which is insoluble in water and in the form of solid, can be obtained. Water present in the phosphoric compound represented by Chemical Formula 1 can be completely removed using the depressurizing oven, or other suitable means.

Flame Retardant Thermoplastic Resin Composition

The present invention provides a flame retardant thermoplastic resin composition using the phosphoric compound represented by the Chemical Formula 1. The resin composition comprises the thermoplastic resin and the phosphoric compound represented by Chemical Formula 1 or a mixture thereof.

In exemplary embodiments of the present invention, the flame retardant thermoplastic resin composition comprises about 100 parts by weight of the thermoplastic resin, and about 0.5 to about 30 parts by weight, for example about 2 to about 25 parts by weight, and as another example about 2.5 to about 20 parts by weight, of the phosphoric compound represented by Chemical Formula 1 or a mixture thereof, based on 100 parts by weight of the thermoplastic resin.

In some embodiments, the phosphoric compound represented by Chemical Formula 1 or a mixture thereof may be present in an amount of about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments of the present invention, the amount of the phosphoric compound represented by Chemical Formula 1 or a mixture thereof can be in a range from about any of the foregoing amounts to about any other of the foregoing amounts.

When the flame retardant thermoplastic resin composition includes the phosphoric compound represented by Chemical Formula 1 or a mixture thereof in an amount of less than about 0.5 parts by weight, the resin composition may not obtain sufficient flame retardancy. On the other hand, when the amount of the phosphoric compound represented by Chemical Formula 1 or a mixture thereof is more than about 30 parts by weight, fundamental properties of the resin composition may be deteriorated.

Examples of the thermoplastic resin used in the present invention are not especially limited. Examples of the thermoplastic resin can include, without limitation, aromatic vinyl polymer resins, polyphenylene ether resins, polyphenylene sulfide resins, polyalkyl(meth)acrylate resins, polycarbonate resins, polyolefin-based resins, polyester resins, polyamide resins, and the like, and combinations thereof may be used.

Examples of the aromatic vinyl polymer resin may include without limitation polystyrene resin (PS), rubber modified polystyrene resin (HIPS), aromatic vinyl-vinyl cyanide graft copolymer resin (ABS), vinyl cyanide-aromatic vinyl copolymer resin (SAN), and the like, and combinations thereof. Examples of the polyolefin-based resin may include without limitation polyethylene, polypropylene, and the like, and combinations thereof. Examples of the polyester resin may include without limitation polyethylene terephthalate, polybutylene terephthalate, and the like, and combinations thereof. Examples of the polyalkyl(meth)acrylate resin may include without limitation polymethylmethacrylate (PMMA) resin, and the like, and combinations thereof.

In exemplary embodiments, the thermoplastic resin may include an aromatic vinyl polymer resin such as polystyrene resin (PS), rubber modified polystyrene resin (HIPS), aromatic vinyl-vinyl cyanide graft copolymer resin (such as an acrylonitrile-butadiene-styrene or ABS resin), or vinyl cyanide-aromatic vinyl copolymer resin (such as a styrene-acrylonitrile or SAN resin); polyphenylene ether resin, polyphenylene sulfide resin, polycarbonate resin, polyethylene resin, polypropylene resin, polyethylene terephthalate, polybutylene terephthalate, polymethylmethacrylate resin, polyamide resin, and the like may be used. The thermoplastic resin may be used alone or in combination thereof.

In exemplary embodiments of the present invention, the resin composition comprises a mixture comprising (A) an aromatic vinyl polymer resin and (B) a polyphenylene ether resin as the thermoplastic resin. For example, the resin composition can include 100 parts by weight of a mixture comprising (A) about 80 to about 95% by weight of the aromatic vinyl polymer resin and (B) about 5 to about 20% by weight of the polyphenylene ether resin, and about 0.5 to about 30 parts by weight of the phosphoric compound represented by Chemical Formula 1 or a mixture thereof.

In some embodiments, the aromatic vinyl polymer resin may be present in an amount of about 80, 81, 82, 83, 84, 85, 86, 87, 88, 89, 90, 91, 92, 93, 94, or 95% by weight. Further, according to some embodiments of the present invention, the amount of the aromatic vinyl polymer resin can be in a range from about any of the foregoing amounts to about any other of the foregoing amounts.

In some embodiments, the polyphenylene ether resin may be present in an amount of about 5, 6, 7, 8, 9, 10, 11, 12, 13, 14, 15, 16, 17, 18, 19, or 20% by weight. Further, according to some embodiments of the present invention, the amount of the polyphenylene ether resin can be in a range from about any of the foregoing amounts to about any other of the foregoing amounts.

In some embodiments, the phosphoric compound represented by Chemical Formula 1 or a mixture thereof may be present in an amount of about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments of the present invention, the amount of the phosphoric compound represented by Chemical Formula 1 or a mixture thereof can be in a range from about any of the foregoing amounts to about any other of the foregoing amounts.

(A) Aromatic Vinyl Polymer Resin.

In exemplary embodiments of the present invention, the aromatic vinyl polymer resin (A) may be a homopolymer of an aromatic vinyl monomer or a copolymer of one or more aromatic vinyl monomers and optionally one or more rubber monomers. Also, the aromatic vinyl polymer resin (A) can further comprise one or more other monomers, such as a (meth)acrylic acid alkyl ester monomer, unsaturated nitrile (also referred to herein as vinyl cyanide) monomer, and the like, and mixtures thereof.

Examples of the aromatic vinyl monomer include without limitation styrene, α-methyl styrene, para-methyl styrene, and the like. The aromatic vinyl monomer may be used singly or in the form of combinations of two or more thereof. In exemplary embodiments, the aromatic vinyl monomer includes styrene.

The (meth)acrylic acid alkyl ester monomer can be a (meth)acrylic acid alkyl ester having a C1 to C10 alkyl group. Examples of the (meth)acrylic acid alkyl ester monomer may include without limitation methyl methacrylate, ethyl methacrylate, propyl methacrylate, butyl methacrylate, pentyl methacrylate, hexyl methacrylate, heptyl methacrylate, octyl methacrylate, methyl acrylate, ethyl acrylate, propyl acrylate, butyl acrylate, pentyl acrylate, hexyl acrylate, heptyl acrylate, octyl acrylate, ethyl hexyl acrylate and the like. The (meth)acrylic acid alkyl ester monomer may be used singly or in the form of combinations of two or more thereof.

Examples of the vinyl cyanide monomer include without limitation acrylonitrile, methacrylonitrile, ethacrylonitrile, and the like. The vinyl cyanide monomer may be used singly or in the form of combinations of two or more thereof. In exemplary embodiments, the vinyl cyanide monomer includes acrylonitrile.

In exemplary embodiments of the present invention, the aromatic vinyl polymer resin can include polystyrene resin (PS), rubber modified polystyrene resin (HIPS), aromatic vinyl-vinyl cyanide graft copolymer resin (ABS), vinyl cyanide-aromatic vinyl copolymer resin (SAN), and the like, and combinations thereof.

Examples of the rubber can include without limitation butadiene-based rubber, isoprene based rubber, a copolymer of butadiene and styrene, alkyl(meth)acrylate rubber, and the like, and mixtures thereof. The rubber can be present in an amount of about 3 to about 30% by weight, for example about 5 to about 15% by weight, based on the total weight of the aromatic vinyl polymer resin (A).

The aromatic vinyl monomer can be used in an amount of about 70 to about 97% by weight, for example about 85 to about 95% by weight, based on the total weight of the aromatic vinyl polymer resin (A).

The aromatic vinyl polymer resin (A) may also include other monomer(s) such as but not limited to vinyl cyanide monomers such as acrylonitrile, acrylic acid, methacrylic acid, maleic acid anhydride, N-substituted maleimide, and the like, in order to impart properties such as chemical resistance, processability, flame retardancy, and the like. The other monomer maybe used in an amount of about 40% by weight or less, based on the total weight of the aromatic vinyl polymer resin (A).

The aromatic vinyl polymer resin (A) can be manufactured by polymerization in the presence of a polymerization initiator or by thermal polymerization without a polymerization initiator. Examples of the polymerization initiator include without limitation peroxide-based initiators such as benzoyl peroxide, t-butyl hydroperoxide, acetyl peroxide, cumen hydroperoxide, and the like; azo-based initiators such as azobisisobutyronitrile, and the like; and combinations thereof.

The aromatic vinyl polymer resin (A) can manufactured using conventional techniques, such as but not limited to bulk polymerization, suspension polymerization, emulsion polymerization, and the like, and combinations thereof.

In the blend comprising the aromatic vinyl polymer resin (A) and the polyphenylene ether resin (B), the size of the rubber phase particle can be about 0.1 to about 2.0 µm for the best properties.

The mixture of the aromatic vinyl polymer resin (A) and the polyphenylene ether resin (B) can include the aromatic vinyl polymer resin (A) in an amount of about 80 to about 95% by weight, for example about 80 to about 90% by weight, based on the total weight of (A)+(B). In some embodiments, the aromatic vinyl polymer resin may be present in an amount of about 80, 81, 82, 83, 84, 85, 86, 87, 88, 89, 90, 919, 92, 93, 94, or 95% by weight. Further, according to some embodiments of the present invention, the amount of the aromatic vinyl polymer resin can be in a range from about any of the foregoing amounts to about any other of the foregoing amounts.

(B) Polyphenylene Ether Resin

In exemplary embodiments of the present invention, a polyphenylene ether resin (B) can be used in combination with the aromatic vinyl polymer resin (A) which can improve flame retardancy and heat resistance of the thermoplastic resin composition.

Examples of the polyphenylene ether resin (B) include without limitation poly(2,6-dimethyl-1,4-phenylene)ether, poly(2,6-diethyl-1,4-phenylene)ether, poly(2,6-dipropyl-1,4-phenylene)ether, poly(2-methyl-6-ethyl-1,4-phenylene)ether, poly(2-methyl-6-propyl-1,4-phenylene)ether, poly(2-ethyl-6-propyl-1,4-phenylene)ether, poly(2,6-diphenyl-1,4-phenylene)ether, copolymer of poly(2,6-dimethyl-1,4-phenylene)ether and poly(2,3,6-trimethyl-1,4-phenylene)ether, copolymer of poly(2,6-dimethyl-1,4-phenylene)ether and poly(2,3,5-triethyl-1,4-phenylene)ether, and the like. The polyphenylene ether resin may be used alone or in combination thereof. In exemplary embodiments, a copolymer of poly(2,6-dimethyl-1,4-phenylene)ether and poly(2,3,6-trimethyl-1,4-phenylene)ether or poly(2,6-dimethyl-1,4-phenylene)ether can be used.

The degree of polymerization of the polyphenylene ether resin (B) is not limited. In exemplary embodiments, the degree of polymerization of the polyphenylene ether resin measured in chloroform solvent at 25° C. can be about 0.2 to about 0.8 in view of heat stability and workability of the thermoplastic resin composition.

The mixture of aromatic vinyl polymer resin (A) and polyphenylene ether resin (B) can include the polyphenylene ether resin (B) in amount of about 5 to about 20% by weight, for example about 10 to about 20% by weight, based on the total weight of (A)+(B). In some embodiments, the polyphenylene ether resin may be present in an amount of about 5, 6, 7, 8, 9, 10, 11, 12, 13, 14, 15, 16, 17, 18, 19, or 20% by weight. Further, according to some embodiments of the present invention, the amount of the polyphenylene ether resin can be in a range from about any of the foregoing amounts to about any other of the foregoing amounts.

When the amount of the polyphenylene ether resin (B) is less than about 5% by weight, flame retardancy of the resin composition may be deteriorated. On the other hand, when the amount of the polyphenylene ether resin (B) is more than about 20% by weight, moldability of the resin composition may be deteriorated.

In other exemplary embodiments of the present invention, the thermoplastic resin composition may further include an aromatic phosphoric acid ester compound (D1), an alkyl phosphinic acid metal salt compound (D2), or a mixture thereof, in order to improve flame retardancy.

The thermoplastic resin composition may include the aromatic phosphoric acid ester compound (D1), alkyl phosphinic acid metal salt compound (D2), or mixture thereof in amount of about 1 to about 25 parts by weight, for example about 5 to about 20 parts by weight, and as another example about 10 to about 15 parts by weight, based on 100 parts by weight of the thermoplastic resin. In some embodiments, the thermoplastic resin composition may include the aromatic phosphoric acid ester compound (D1), alkyl phosphinic acid metal salt compound (D2), or mixture thereof in an amount of about 1, 2, 3, 4, 5, 6, 7, 8, 9, 10, 11, 12, 13, 14, 15, 16, 17, 18, 19, 20, 21, 22, 23, 24, or 25 parts by weight. Further, according to some embodiments of the present invention, the amount of the aromatic phosphoric acid ester compound (D1), alkyl phosphinic acid metal salt compound (D2), or mixture thereof can be in a range from about any of the foregoing amounts to about any other of the foregoing amounts.

When the amount of the aromatic phosphoric acid ester compound (D1), alkyl phosphinic acid metal salt compound (D2), or mixture thereof is less than about 1 part by weight, the resin composition may not obtain sufficient flame retardancy. On the other hand, when the amount of the aromatic phosphoric acid ester mixture (D1), alkyl phosphinic acid metal salt compound (D2), or mixture thereof is more than about 25 parts by weight, properties such as impact strength may be deteriorated.

(D1) Aromatic Phosphoric Acid Ester Compound

The aromatic phosphoric acid ester compound (D1) that can be used in the thermoplastic resin composition according to exemplary embodiments of the present invention can have a structure of the following Chemical Formula 6.

[Chemical Formula 6]

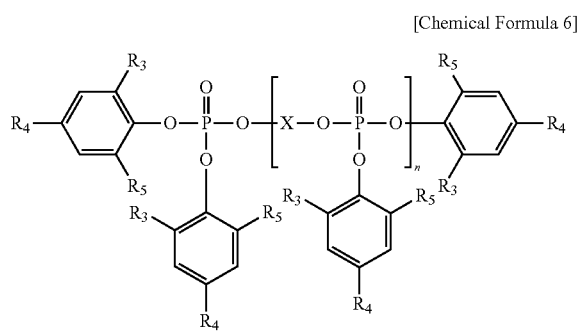

In Chemical Formula 6, $R_3$, $R_4$, and $R_5$ are the same or different and are independently hydrogen or $C_1$-$C_4$ alkyl; X is $C_6$-$C_{20}$ aryl or $C_1$-$C_4$ alkyl-substituted $C_6$-$C_{20}$ aryl and is derived from dialcohol of resorcinol, hydroquinol, or bisphenol-A; and n is an integer of 0 to 4.

Examples of the aromatic phosphoric acid ester compound (D1) are as follows. When n is 0 in Chemical Formula 6, examples of the compound represented by Chemical Formula 6 include without limitation triphenyl phosphate, tri(2,6-dimethyl) phosphate, and the like. When n is 1 in Chemical Formula 6, examples of the compound represented by Chemical Formula 6 include without limitation resorcinol bis (diphenyl) phosphate, resorcinol bis(2,6-dimethylphenyl) phosphate, resorcinol bis(2,4-ditertiarybutylphenyl) phosphate, hydroquinol bis(2,6-dimethylphenyl) phosphate, hydroquinol bis(2,4-ditertiarybutylphenyl) phosphate, and the like. The aromatic phosphoric acid ester compound can be used alone or in combination thereof.

(D2) Alkyl Phosphinic Acid Metal Salt Compound

The alkyl phosphinic acid metal salt compound (D2) that can be used in the thermoplastic resin composition according to exemplary embodiments of the present invention can have a structure of the following Chemical Formula 7.

[Chemical Formula 7]

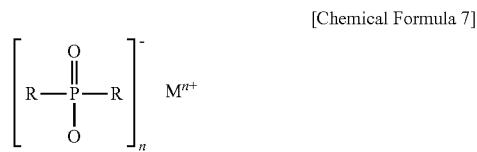

In Chemical Formula 7, each R is the same or different and is independently $C_1$-$C_6$ alkyl, $C_4$-$C_6$ cycloalkyl, or $C_6$-$C_{10}$ aryl; M is a metal of Al, Zn, Mg or Ca; and n is an integer of 2 or 3.

In exemplary embodiments, each R is independently methyl, ethyl, propyl, butyl or phenyl, and M is Al or Zn.

An example of the alkyl phosphinic acid metal salt compound (D2) may include without limitation diethyl phosphinic acid aluminum metal salt.

The average diameter of the alkyl phosphinic acid metal salt compound (D2) can be about 10 μm or less, for example about 0.01 to about 10 μm. When the average diameter of the alkyl phosphinic acid metal salt compound (D2) is more than about 10 μm, the impact strength and flame retardancy of the resin composition may be deteriorated. On the other hand, when the average diameter of the alkyl phosphinic acid metal salt compound (D2) is less than about 0.01 μm, it may be difficult to make the product, and the extrusion or injection processability of the resin composition may be deteriorated.

In other exemplary embodiments of the present invention, the thermoplastic resin composition may further include one or more additives, depending on its use. Examples of the additives may include without limitation plasticizers, heat stabilizers, antioxidants, anti-dripping agents, compatibilizers, light-stabilizers, pigments, dyes, inorganic fillers, and the like. Examples of the inorganic fillers may include without limitation asbestos, glass fibers, talc, ceramic, sulfates, and the like. The additives can be used alone or in combination thereof. The thermoplastic resin composition of the invention can include one or more additives in an amount of about 30 parts by weight or less, for example about 0.001 to about 30 parts by weight, based on 100 parts by weight of the thermoplastic resin.

The thermoplastic resin composition according to the present invention can be manufactured by conventional methods known in the art. In exemplary embodiments, after the above-stated components are mixed with (optional) additives, the thermoplastic resin composition can be manufactured in the form of pellets by melt extruding in an extruding machine.

The flame retardant thermoplastic resin composition according to the present invention can be used in the manufacture of various products due to its excellent flame retardancy. For example, the flame retardant thermoplastic resin composition can be used to produce exterior materials for electric/electronic goods such as housings for televisions, computers, audio equipment, air conditioners, office automation equipment, and the like, to which strict flame retardancy regulations are required.

The method for preparing the plastic products from the flame retardant thermoplastic resin composition according to the present invention is not limited. For example, the products can be made using conventional molding processes known in the art, such as extrusion molding, injection molding, blow molding, casting molding, and the like. These methods can be easily carried out by a person of ordinary skill in the art.

The invention may be better understood by reference to the following examples which are intended for the purpose of illustration and are not to be construed as in any way limiting the scope of the present invention, which is defined in the claims appended hereto.

EXAMPLES

Example 1

Preparation of a Phosphoric Compound (C1)

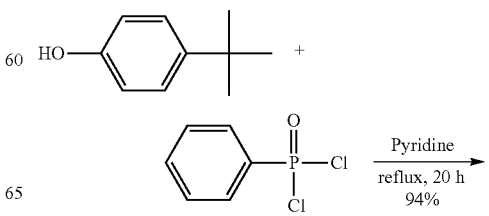

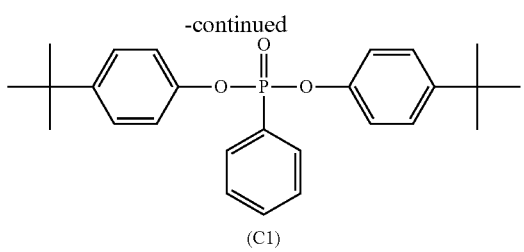

(C1)

Figure 2:
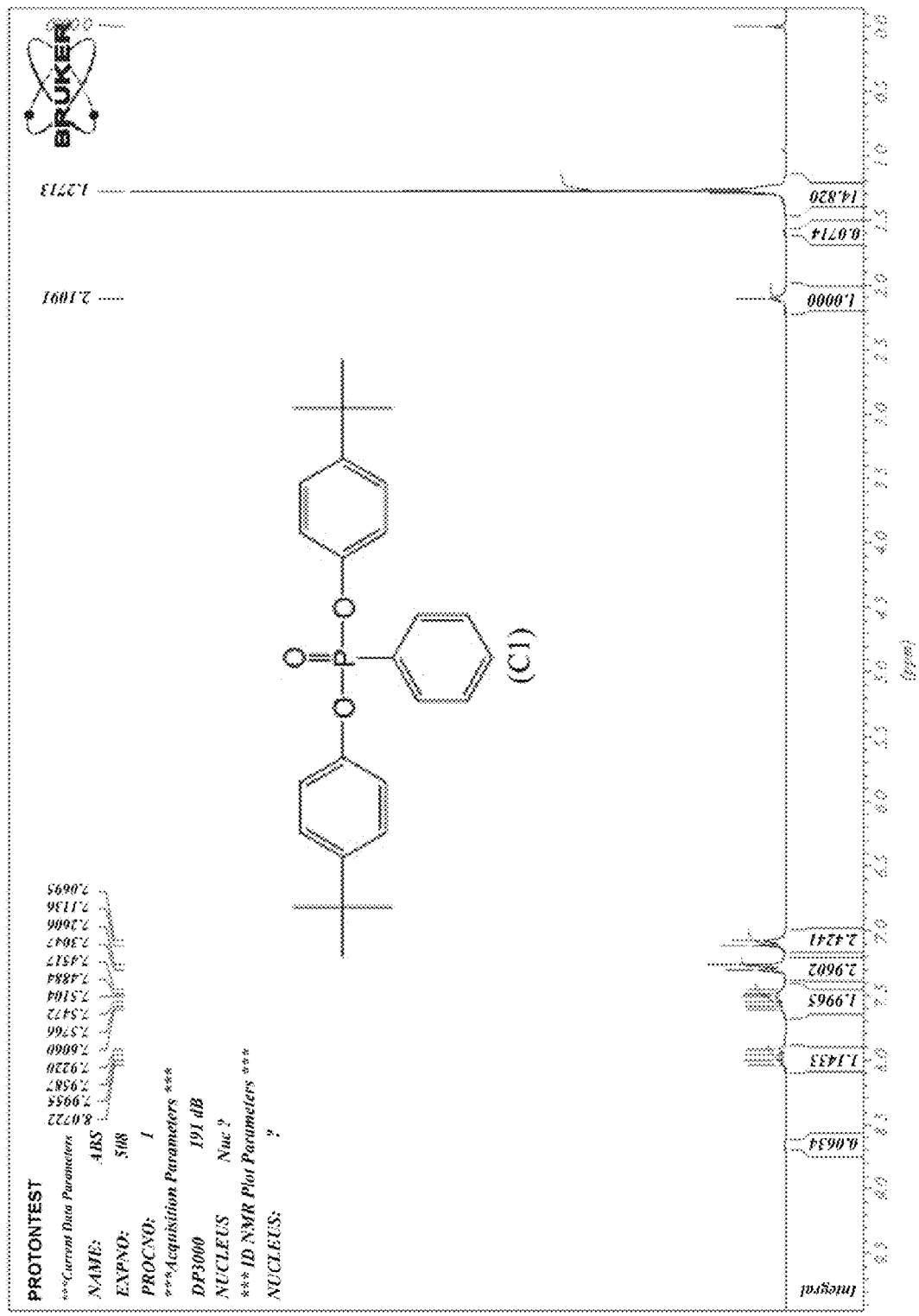
FIG. 2 is a $^1$H-NMR spectrum of phosphoric compound (C1) prepared in Example 1.

4-tert-butyl phenol (60 g, 0.40 mol), phenyl phosphonic dichloride (43 g, 0.20 mol), and pyridine (400 mL, 4.97 mol) are added into a reactor, refluxed and stirred at 140° C. for about 20 hours. The temperature of the reactor is cooled down to room temperature and then the unreacted pyridine is removed by depressurizing the reaction product using a rotary distillation apparatus. 500 mL of distilled water is added into the reaction product, which is in the form of solid by removing the unreacted pyridine, the resulting solution is stirred for 1 hour to dissolve pyridine hydrochloride produced during the reaction in the water layer, and the resulting solution is filtered to obtain a water-insoluble solid compound (C1). The filtered solid compound (C1) is dried for 24 hours in an oven under reduced pressure to obtain a pure white solid of bis(4-tert-butylphenyl)phenyl phosphonate (C1) (79 g, yield: 96%). The resultant compound (C1) is analyzed by GC-MS and $^1$H-NMR, and the results are shown in FIGS. 1 and 2, respectively.

Example 2

Preparation of a Phosphoric Compound (C2)

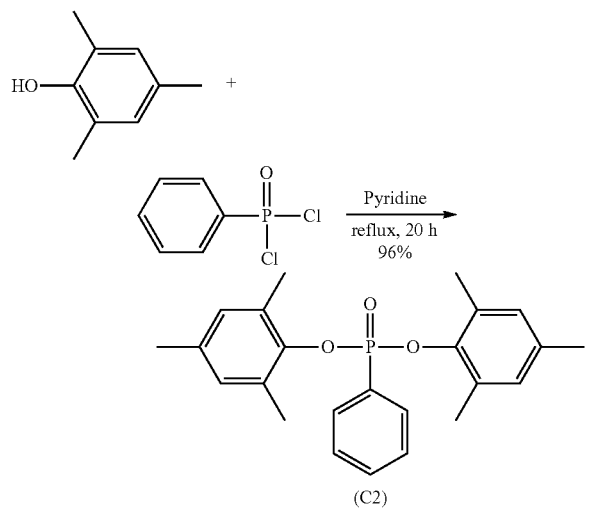

(C2)

Figure 3:
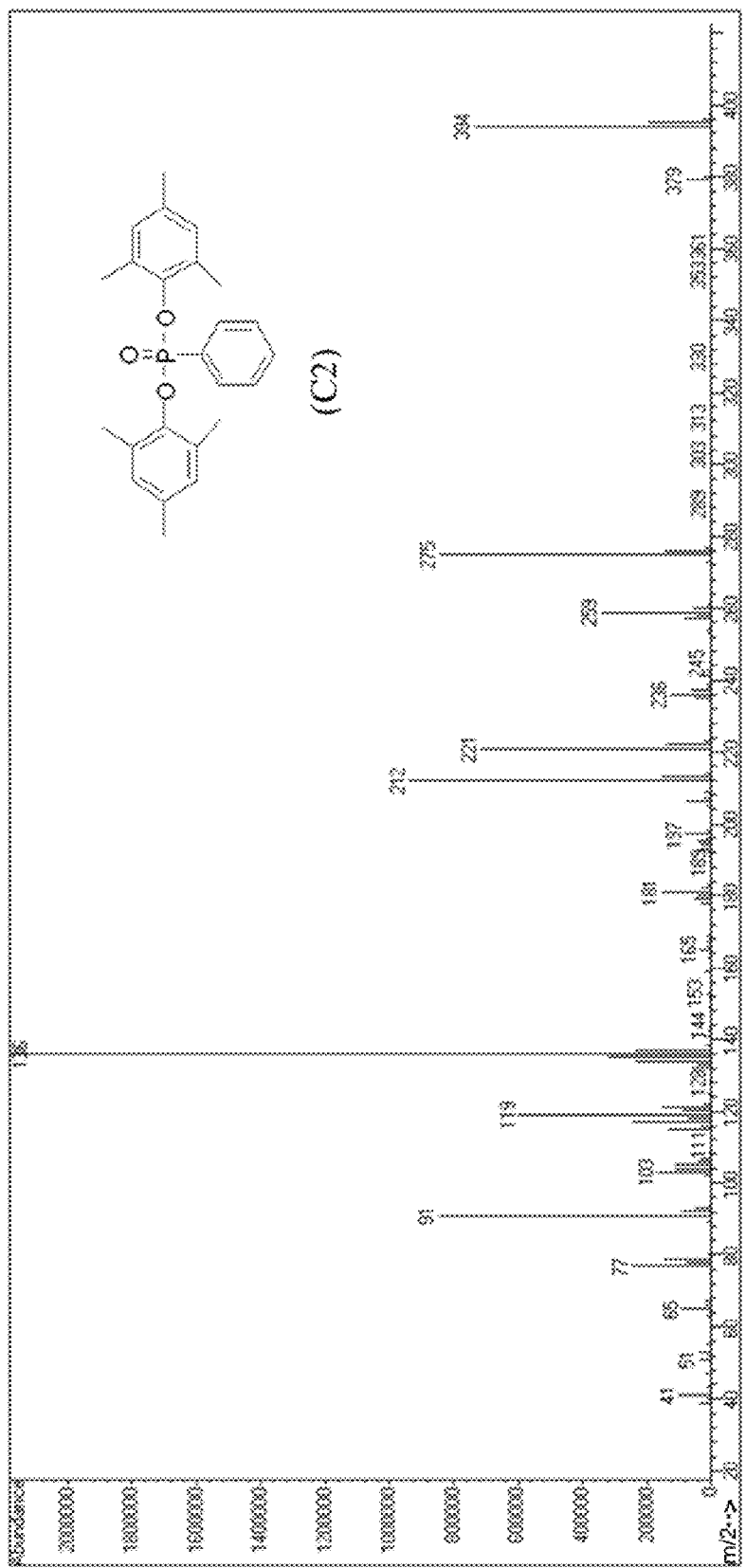
FIG. 3 is a GC-MS chromatogram of phosphoric compound (C2) prepared in Example 2.
Figure 4:
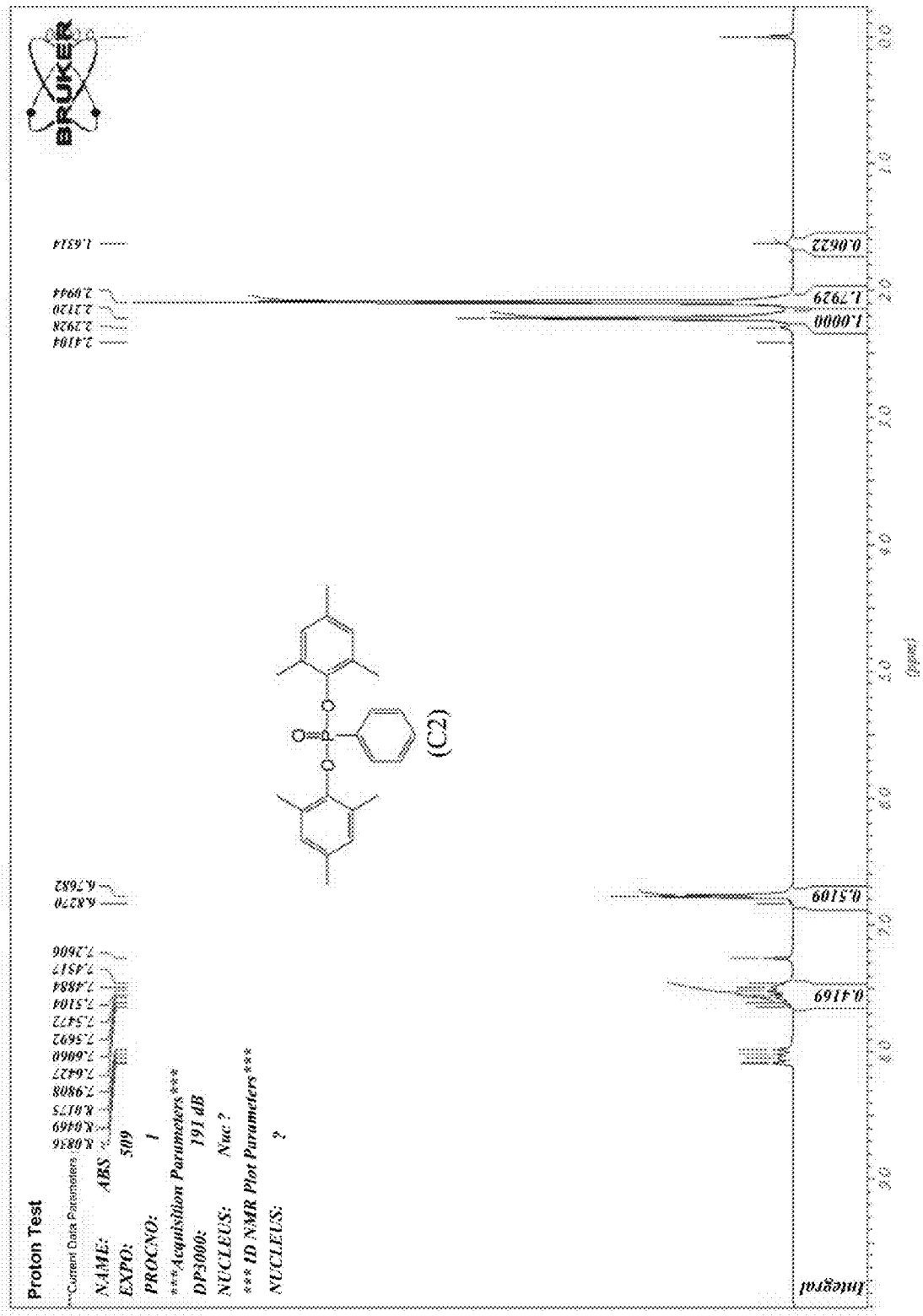
FIG. 4 is a $^1$H-NMR spectrum of phosphoric compound (C2) prepared in Example 2.

2,4,6-trimethyl phenol (54 g, 0.40 mol), phenyl phosphonic dichloride (43 g, 0.20 mol), and pyridine (400 mL, 4.97 mol) are added into a reactor, refluxed, and stirred at 140° C. for about 20 hours. The temperature of the reactor is cooled down to room temperature and then the unreacted pyridine is removed by depressurizing the reaction product using a rotary distillation apparatus. 500 mL of distilled water is added into the reaction product, which is in the form of solid by removing the unreacted pyridine, the resulting solution is stirred for 1 hour to dissolve pyridine hydrochloride produced during the reaction in the water layer, and the resulting solution is filtered to obtain a water-insoluble solid compound (C2). The filtered solid compound (C2) is dried for 24 hours in an oven under reduced pressure to obtain a pure white solid of bis(2,4,6-trimethylphenyl)phenyl phosphonate (C2) (75.7 g, yield: 96%). The resultant compound (C2) is analyzed by GC-MS and $^1$H-NMR, and the results are shown in FIGS. 3 and 4, respectively.

Preparation of Flame Retardant Thermoplastic Resin Composition

Specifications of each components used in the following examples and comparative examples are as follows.

(A) Aromatic Vinyl Polymer Resin

Rubber modified styrene resin made by Cheil Industries Inc. of Korea (product name: HG-1760S) is used.

(B) Polyphenylene Ether Resin

Poly(2,6-dimethyl-1,4-phenylene)ether made by Mitsubishi Engineering Plastic Company of Japan (product name: PX-100F) is used.

(C) Phosphoric Compound (C1) Bis(4-tert-butylphenyl)phenyl phosphonate prepared in Example 1 is used.

(C2) Bis(2,4,6-trimethylphenyl)phenyl phosphonate prepared in Example 2 is used.

(D1) Aromatic Phosphoric Acid Ester Compound

Bis(dimethylphenyl) phosphate bisphenol A made by Daihachi Chemical Industry Co., Ltd. of Japan (product name: CR741S) is used.

(D2) Alkyl Phosphinic Acid Metal Salt Compound

Diethyl Phosphinic acid aluminum metal salt made by Clariant Company (product name: Exolit OP930) is used. The average diameter is 5 μM.

Examples 3 to 8

The components are added into a conventional mixer in an amount as described in the following Table 1, and the mixture is extruded through a conventional twin screw extruder at a temperature range of 200 to 280° C. to prepare a product in pellet form. The pellets are dried at 80° C. for 2 hours and then molded into test specimens in a 6 oz injection molding machine at 180 to 280° C. with a mold temperature of 40 to 80° C.

The flame retardancy is measured in accordance with UL 94 VB for the specimens having a thickness of about ⅛". The results of Examples 3 to 8 are shown in Table 1.

Comparative Examples 1 to 2

Comparative Examples 1 to 2 are prepared in the same manner as the Examples above except each component is used in a different amount. The results of Comparative Examples 1 to 2 are shown in Table 1.

TABLE 1

|  |  | Examples | | | | | | Comparative Examples | |
|---|---|---|---|---|---|---|---|---|---|
|  |  | 3 | 4 | 5 | 6 | 7 | 8 | 1 | 2 |
| (A) |  | 85 | 85 | 85 | 85 | 85 | 85 | 85 | 85 |
| (B) |  | 15 | 15 | 15 | 15 | 15 | 15 | 15 | 15 |
| (C) | (C1) | 20 | — | 5 | — | 2.5 | — | — | — |
|  | (C2) | — | 20 | — | 5 | — | 2.5 | — | — |
| (D) | (D1) | — | — | 15 | 15 | 10 | 10 | 20 | 15 |
|  | (D2) | — | — | — | — | 2.5 | 2.5 | — | 5 |
| First average combustion time (⅛", sec) | | 37.5 | 23.0 | 27.7 | 20.9 | 15.2 | 8.5 | 41.3 | 41.5 |
| Second average combustion time (⅛", sec) | | 27.0 | 24.7 | 24.5 | 23.8 | 19.8 | 15.1 | 31.5 | 10.2 |

As shown in Table 1, it can be seen that Examples 3 to 4 using only the flame retardant phosphoric compound of the invention and Examples 5 to 8 using the flame retardant phosphoric compound of the invention as well as a conventional phosphoric flame retardant exhibit excellent flame retardant properties, as compared to Comparative Examples 1 to 2 using only a conventional phosphoric flame retardant.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A phosphoric compound represented by the following Chemical Formula 1:

[Chemical Formula 1]

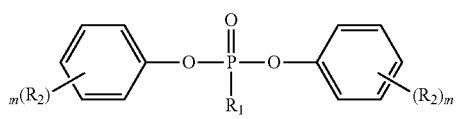

wherein $R_1$ is phenyl and each $R_2$ is the same or different and is independently $C_1$-$C_6$ alkyl or aryl; and each m is 3.

2. The phosphoric compound of claim 1, wherein each $R_2$ is independently $C_1$-$C_6$ alkyl.

3. The phosphoric compound of claim 1, wherein the phosphoric compound is bis(2,4,6-trimethylphenyl)phenyl phosphonate represented by the following Chemical Formula 3

[Chemical Formula 3]

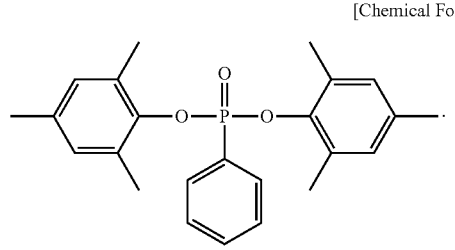

4. A method for preparing a phosphoric compound represented by the following Chemical Formula 1

[Chemical Formula 1]

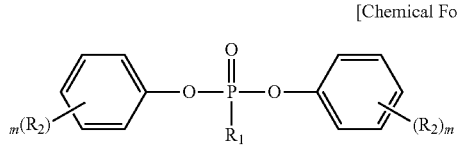

wherein $R_1$ is phenyl and each $R_2$ is the same or different and is independently $C_1$-$C_6$ alkyl or aryl; and each m is the same or different and is independently an integer of 1 to 3, the method comprising:

reacting a compound or a combination of compounds represented by the following Chemical Formula 4 with a compound represented by the following Chemical Formula 5 in the presence of an organic amine compound:

[Chemical Formula 4]

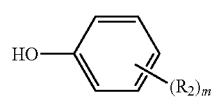

wherein each $R_2$ is the same or different and is independently $C_1$-$C_6$ alkyl or aryl; and each m is the same or different and is independently an integer of 1 to 3,

[Chemical Formula 5]

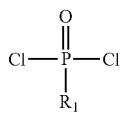

wherein $R_1$ is phenyl.

5. The method of claim 4, wherein said organic amine compound is pyridine, triethylamine, or a mixture thereof.

6. The method of claim 4, comprising reacting the compound represented by Chemical Formula 4 and the compound represented by Chemical Formula 5 in a molar ratio of about 2:1 to about 3:1.

7. The method of claim 4, wherein the molar ratio of the organic amine compound to the compound represented by Chemical Formula 5 is about 2:1 to about 50:1.

8. The method of claim 4, comprising:
   reacting the compound or combination of compounds represented by Chemical Formula 4 with the compound represented by Chemical Formula 5 in the presence of an organic amine compound for about 10 to about 30 hours at a temperature of about 120 to about 160° C. while stirring and refluxing the reaction mixture;
   removing unreacted organic amine compound by depressurizing the reaction product obtained by the reaction; and
   filtering and drying the reaction product, from which the unreacted organic amine compound was removed, after washing the reaction product.

9. A flame retardant represented by the following Chemical Formula 1:

[Chemical Formula 1]

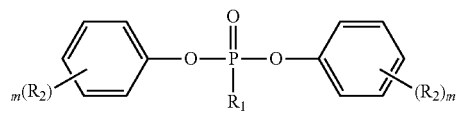

wherein $R_1$ is phenyl and each $R_2$ is the same or different and is independently $C_1$-$C_6$ alkyl or aryl; and each m is 3.

10. A flame retardant thermoplastic resin composition comprising:
   100 parts by weight of a thermoplastic resin; and
   about 0.5 to about 30 parts by weight of a phosphoric compound represented by the following Chemical Formula 1:

[Chemical Formula 1]

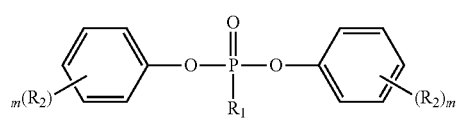

wherein $R_1$ is phenyl and each $R_2$ is the same or different and is independently $C_1$-$C_6$ alkyl or aryl; and each m is 3.

11. The flame retardant thermoplastic resin composition of claim 10, wherein the phosphoric compound is bis(2,4,6-trimethylphenyl)phenyl phosphonate represented by the following Chemical Formula 3

[Chemical Formula 3]

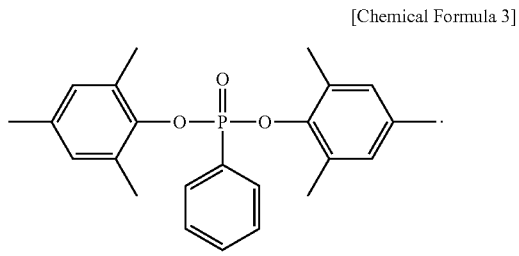

12. The flame retardant thermoplastic resin composition of claim 10, wherein the thermoplastic resin comprises an aromatic vinyl polymer resin including polystyrene resin (PS), rubber modified polystyrene resin (HIPS), aromatic vinyl-vinyl cyanide graft copolymer resin (ABS), vinyl cyanide-aromatic vinyl copolymer resin (SAN); polyphenylene ether resin, polyphenylene sulfide resin, polycarbonate resin, polyethylene resin, polypropylene resin, polyethylene terephthalate, polybutylene terephthalate, polymethylmethacrylate, polyamide resin, or a mixture thereof.

13. The flame retardant thermoplastic resin composition of claim 10, wherein the thermoplastic resin comprises (A) about 80 to about 95% by weight of an aromatic vinyl polymer resin and (B) about 5 to about 20% by weight of a polyphenylene ether resin.

14. The flame retardant thermoplastic resin composition of claim 10, further comprising about 1 to about 25 parts by weight of (D1) an aromatic phosphoric acid ester compound, (D2) an alkyl phosphinic acid metal salt compound, or a mixture thereof, based on 100 parts by weight of the thermoplastic resin.

15. The flame retardant thermoplastic resin composition of claim 14, wherein the aromatic phosphoric acid ester compound (D1) has a structure of the following Chemical Formula 6:

[Chemical Formula 6]

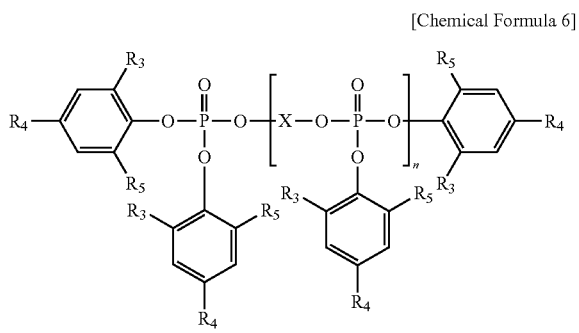

wherein $R_3$, $R_4$, and $R_5$ are the same or different and are each independently hydrogen or $C_1$-$C_4$ alkyl; X is $C_6$-$C_{20}$ aryl or $C_1$-$C_4$ alkyl-substituted $C_6$-$C_{20}$ aryl and is derived from a dialcohol of resorcinol, hydroquinol, or bisphenol-A; and n is an integer of 0 to 4.

16. The flame retardant thermoplastic resin composition of claim 14, wherein the alkyl phosphinic acid metal salt compound (D2) has a structure of the following Chemical Formula 7:

[Chemical Formula 7]

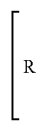

wherein each R is the same or different and is independently $C_1$-$C_6$ alkyl, $C_4$-$C_6$ cycloalkyl, or $C_6$-$C_{10}$ aryl; M is a metal of Al, Zn, Mg or Ca; and n is an integer of 2 or 3.

17. The flame retardant thermoplastic resin composition of claim 10, further comprising an additive selected from the group consisting of plasticizers, heat stabilizers, antioxidants, anti-dripping agents, compatibilizers, light-stabilizers, pigments, dyes, inorganic fillers and mixtures thereof.

18. The method of claim 4, wherein each $R_2$ is independently $C_1$-$C_6$ alkyl.

19. The method of claim 4, wherein the phosphoric compound of Chemical Formula 1 is bis(4-tert-butylphenyl)phenyl phosphonate represented by the following Chemical Formula 2

[Chemical Formula 2]

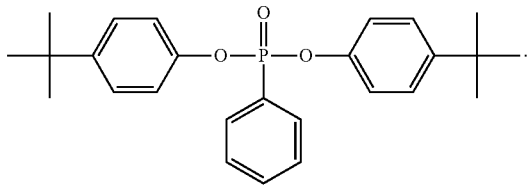

20. The method of claim 4, wherein the phosphoric compound of Chemical Formula 1 is bis(2,4,6-trimethylphenyl) phenyl phosphonate represented by the following Chemical Formula 3

[Chemical Formula 3]

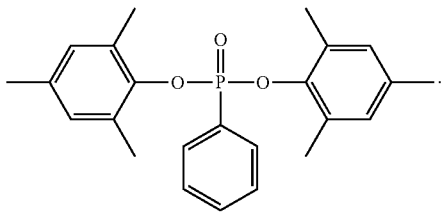

21. The flame retardant thermoplastic resin composition of claim 10, wherein each $R_2$ is independently $C_1$-$C_6$ alkyl.

* * * * *